United States Patent [19]

Francis et al.

[11] Patent Number: 4,758,345

[45] Date of Patent: Jul. 19, 1988

[54] ANAEROBIC MICROBIAL DISSOLUTION OF LEAD AND PRODUCTION OF ORGANIC ACIDS

[75] Inventors: Arokiasamy J. Francis, Middle Island; Cleveland Dodge, Wading River, both of N.Y.; Krishnachetty Chendrayan, Coimbatore Tamil Nadu, India; Helen L. Quinby, Cambridge, Md.

[73] Assignee: The United States of America as represented by the United States Department of Energy, Washington, D.C.

[21] Appl. No.: 39,131

[22] Filed: Apr. 16, 1987

Related U.S. Application Data

[63] Continuation-in-part of Ser. No. 834,675, Feb. 28, 1986, abandoned.

[51] Int. Cl.$^4$ .............................. C02F 3/34; C12P 7/52; C12P 7/54; C12P 7/56
[52] U.S. Cl. .................................... 210/611; 210/912; 435/139; 435/140; 435/141; 435/262; 435/842
[58] Field of Search ............... 210/601, 603, 611, 631, 210/911, 912; 435/139, 253, 262, 140, 141, 822, 842

[56] References Cited

U.S. PATENT DOCUMENTS

| | | | |
|---|---|---|---|
| 3,266,889 | 8/1966 | Duncan et al. ......................... | 75/101 |
| 3,293,597 | 12/1975 | Chakrabarty et al. ......... | 210/611 X |
| 4,467,034 | 8/1984 | Voelskow et al. ................... | 435/139 |
| 4,468,461 | 8/1984 | Bopp ..................................... | 435/253 |
| 4,510,243 | 4/1985 | Haga et al. ........................... | 435/139 |
| 4,519,912 | 5/1985 | Kauffman et al. ................... | 210/611 |

FOREIGN PATENT DOCUMENTS

| | | | |
|---|---|---|---|
| 113215 | 7/1984 | European Pat. Off. ............. | 435/139 |
| 498338 | 1/1976 | U.S.S.R. . | |
| 910815 | 3/1982 | U.S.S.R. . | |

OTHER PUBLICATIONS

Francis et al., "Anaerobic Microbial Dissolution of Metals", BNL Report 36447, presented at the Workshop on Biotechnology for the Mining, Metal-Refining and Fossil Fuel Processing Industries, Rensselaer Polytechnic Institute, Troy, N.Y., May 28-30, 1985.

Francis, "Anaerobic Microbial Dissolution of Toxic Metals in Subsurface Environments", BNL Report 36571, presented at the DOE International Series of Interactive Seminars (ISIS) on Anaerobic Biogeochemical Processes in Subsurface Environments, Penn State University, May 13-15, 1985.

Francis, "Microbial Transformation of Organic Compounds, Toxic Metals, and Radionuclides in Subsurface Environments", BNL Report 37206, presented at the Workshop on the Effects of Natural Organic Compounds and of Microorganisms on Radionuclide Transport, Paris, France, Jun. 11-12, 1985.

Francis, "Anaerobic Microbial Transformation of Toxic Metals", BNL Report 37250, presented at the Symposium on Transport of Chemicals in the Ground Water and Porous Media, American Institute of Chemical Engineers, Chicago, Ill., Nov., 1985.

*Primary Examiner*—Tom Wyse
*Attorney, Agent, or Firm*—Margaret C. Bogosian; James W. Weinberger; Judson R. Hightower

[57] ABSTRACT

The present invention relates to an anaerobic bacterial culture of *Clostridium sp.* ATCC No. 53464 which solubilizes lead oxide under anaerobic conditions in coal and industrial wastes and therefore presents a method of removing lead from such wastes before they are dumped into the environment. The rate of lead dissolution during logarithmic growth of the bacteria in 40 ml medium containing 3.32 $\mu$moles of lead as lead oxide was 0.042 $\mu$moles ml$^{-1}$ hr$^{-1}$. Dissolution of lead oxide by the bacterial isolate is due to the production of metabolites and acidity in the culture medium. The major metabolites are acetic, butyric and lactic acid. *Clostridium sp.* ATCC No. 53464 can be used in the recovery of strategic metals from ores and wastes and also for the production of lactic acid for commercial purposes. The process yields large quantities of lactic acid as well as lead complexed in a stable form with said acids.

4 Claims, 3 Drawing Sheets

ANAEROBIC MICROBIAL DISSOLUTION OF LEAD AND PRODUCTION OF ORGANIC ACIDS

The U.S. Government has rights in this invention pursuant to Contract Number DE-AC02-76CH00016, between the U.S. Department of Energy and Associated Universities Inc.

RELATED APPLICATIONS

This application is a continuation-in-part application of co-pending application Ser. No. 834,675 filed Feb. 28, 1986, now abandoned.

BACKGROUND OF THE INVENTION

A major national concern in the subsurface disposal of energy waste is the contamination of ground and surface waters by waste leachates containing toxic metals such as lead. There is a significant input of lead into terrestrial and aquatic ecosystems from solid waste disposal and from atmospheric deposition of anthropogenic pollutants. Lead is present in coal bottom and fly ash and is also released into the atmosphere from fossil-fuel combustion and from lead smelters. It is believed that lead is present as lead oxide (PbO) in the coal bottom and fly ash. Lead oxide is also released into the atmosphere from automobile emissions. Lead oxide is quite insoluble in water and its presence in terrestrial and aquatic systems poses a serious threat to the safety and ecology of these systems.

Microorganisms play a major role in the transformation of toxic metals present in wastes and affect their mobility in subsurface environments. Microbial activities affect dissolution, mobilization, and immobilization of toxic metals. Of particular concern is the microbial dissolution and remobilization of lead compounds in oxic and anoxic environments. Patterson [Marine Chemistry, 2, 69, 1984] observed the release of lead in seawater from the adsorbed to dissolved species after storage for three months. Bruland, et al. [Environ. Sci. Technol., 8, 425–432, 1974] noted that contaminated sediments released a greater fraction of their lead content under anaerobic conditions that did unpolluted sediments. Additionally troubling was the finding by Wong, et al. [Nature, 253, 263–264, 1975] that microorganisms in sediments from several Canadian lakes transformed certain inorganic and organic lead compounds into tetramethyl lead.

Applicants have now found that they can apply the role played by microorganisms in the biogeochemical and ecological cycles of lead in a positive fashion in order to solubilize toxic lead compounds. More particularly, applicants have found that an anaerobic bacterium which was isolated from coal beneficiation residue solubilizes a significant amount of lead oxide and an appreciable amount of lead sulfate. The solubilized metal, probably in the form $Pb^{2+}$ associated as an organic complex, is then bioavailable to the microorganism, being found associated with the cell biomass. In addition, the solubilized metal is immobilized by a polymer-like substance produced by the microorganism.

STATEMENT OF DEPOSIT

The bacterium utilized in the present invention is a nitrogen-fixing Clostridium sp. which has been deposited in the American Type Culture Collection in accordance with the Manual of Patent Examining Procedure and prior to the filing of this application. This deposit assures permanence and availability of the bacterium for at least the life of the patent. This Clostridium sp. has been accorded deposit number ATCC No. 53464.

DETAILED DESCRIPTION OF THE INVENTION

Figure 1:
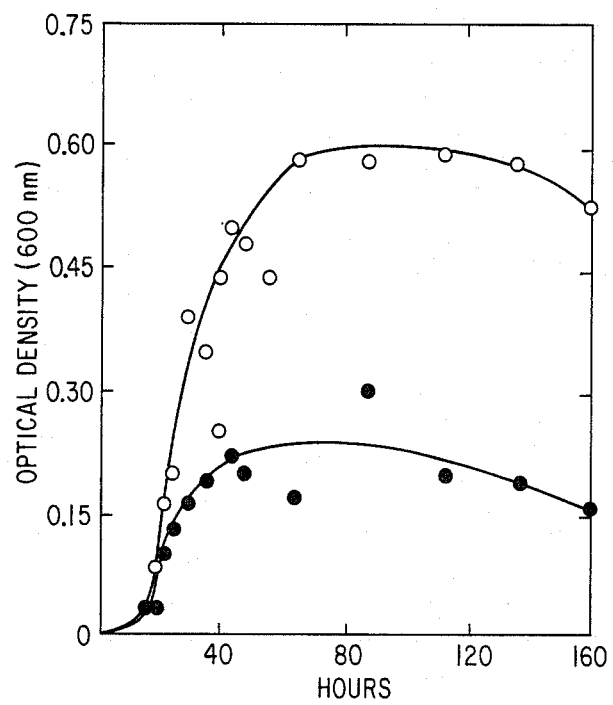
FIG. 1: Growth of Clostridium sp. ATCC 53464 in the presence ( • ) and absence ( ∘ ) of PbO.

The present invention relates to a method of solubilizing lead, in the form of lead oxide, found in industrial wastes, before these wastes are dumped into the environment. The lead is solubilized by dissolving the lead oxide in the wastes through contact with an anaerobic bacterial culture containing the nitrogen-fixing Clostridium sp. ATCC No. 53464 isolated from coal-cleaning waste. The solubilized lead can then be removed from the wastes by chemical separation. It could also be removed by extending the contact period with the bacterial culture. As the culture grows, the solubilized lead is removed from the wastes by bioaccumulation by the microorganism or by immobilization by a polymer-like material produced by the microorganism. At this point, the lead is then removed from the wastes when the waste material is separated from the bacterial culture. If desired, the bacterial culture could be digested at this point to yield relatively pure lead for further industrial use.

The anaerobic bacterial culture containing Clostridium sp. ATCC No. 53464 solubilizes lead oxide under anaerobic conditions. Dissolution of lead oxide is due to the production of organic acids and the lowering of the pH of the growth medium. The rate of dissolution is rapid; for example the rate of lead dissolution during logarithmic growth of bacteria in 40 ml medium containing 3.32 $\mu$moles of lead as lead oxide was 0.042 $\mu$moles ml$^{-1}$hr$^{-1}$. The solubilized lead than affects the growth of Clostridium sp. ATCC 53464 as well as the metabolic end products of glucose fermentation. In its normal fermentation of glucose, Clostridium sp. ATCC 53464 produced acetic, butyric and trace amounts of lactic acid (ratios of approximately 32:63:5), but in the presence of lead oxide, the ratio of organic acids changed (9:38:53) with lactic acid being the major end product.

Therefore, in another embodiment of the present invention, the Clostridium sp. ATCC No. 53464 can be grown in a controlled growth medium to which has been added lead, preferably in the form of lead oxide, in order to promote the production of the valuable organic acid, lactic acid. Clostridium sp. ATCC No. 53464 therefore can be used in the recovery of the strategic metal lead, a metal of industrial importance but toxic when introduced into the land or aquatic environment, from ores and various wastes before such are disposed of in the environment. This microorganism is further useful in the production of lactic acid for commercial purposes, since the lead dissolution process yields large quantities of lactic acid.

EXAMPLE 1

Characterization and Growth of Clostridium sp. ATCC No. 53464

The anaerobic nitrogen-fixing Clostridium sp. ATCC No. 53464 with an acetic and butyric acid fermentation pattern was isolated from coal cleaning waste. This bacterium exhibits the following characteristics: gram-positive, rod shaped, spore forming, anaerobic, saccharolytic, gas producing ($CO_2$ and $H_2$), ferments glucose to acetic and butyric acids and trace amounts of lactic acid, and fixes atmospheric $N_2$.

The anaerobic bacterium ATCC No. 53464 was grown in medium having the following composition: glucose, 5.0 g; $NH_4Cl$, 0.5 g; glycerol phosphate, 0.3 g; $MgSO_4:7H_2O$, 0.2 g; $FeSO_4:7H_2O$, 1.0 mg; $CaCl_2:2H_2O$, 0.5 g; peptone, 0.1 g; yeast extract, 0.1 g; distilled water, 1000 ml; pH 6.8±0.1. The medium was boiled while flushing with nitrogen to remove the dissolved oxygen. It was then dispensed in 100-ml quantities in 125 ml serum bottles inside an anaerobic glove box under a $N_2$ atmosphere. The serum bottles were autoclaved after closing with butyl rubber stoppers and sealed with aluminum caps. The inoculated cultures were incubated with 1.0 ml of 24-hour-old culture at early log phase at about 24±1° C. Growth of the cultures was measured at 600 nm using a Bausch and Lomb Spectronic-20 Spectrophotometer. Numbers of bacteria in the culture sample were obtained by the acridine orange direct counting (AODC) method [Hobbie, *Appl. Environ. Microbiol.*, 33, 1225–1228, 1977].

The pH of the culture samples was measured in the anaerobic glove box using a Beckman Model 21 portable pH meter and a glass Futura II combination electrode.

EXAMPLE 2

Materials and Analytical Methods

Lead oxide (PbO) purity 99.9%, lead sulfate ($PbSO_4$), and lead sulfide (PbS), purity 99.9%, were obtained from Atlantic Equipment Engineers Co., Bergenfield, NJ. Galena (Brushy Creek, Mo.) was obtained from Ward's Natural Sciences Establishment, Rochester, NY. Solid lead compounds were ground to pass through a 250 mesh sieve. Before use, all lead compounds were washed in deionized water several times, dried overnight at 60° C. to remove moisture, and stored in a desiccator. All glassware and serum bottles were washed with 5% $HNO_3$, rinsed in deionized water, and dried in the oven. Lead oxide (12.4 $\mu$moles Pb/100 ml) was added to serum bottles before addition of the medium and then autoclaved.

Soluble lead in the control and inoculated culture media was determined by differential pulse polarography with an EG G polarograph model 174A and model 303SMDE. Prior to lead analysis, the culture samples were filtered through a 0.22-$\mu$m Millex filter (Millipore Co.) and were acidified with $HNO_3$.

Total pressure in the head space was determined by a Wallace and Tiernan pressure gauge (No. 62D-2C-0200) or a Marsh (0–150 psi) pressure gauge attached to a 1 ml hypodermic syringe. Dead volume of the gauges was 3 ml. Total volume of gas produced was calculated from head space volume of sample bottle and total pressure. $CO_2$ and $H_2$ in the head space gas were analyzed using a Perkin-Elmer model 900 gas chromatograph fitted with a stainless steel column (6.1 m×3.2 mm) packed with Silica Gel (60/80, Alltech Assoc. No. 5651) and connected to a thermal conductivity detector. For $CO_2$ determination, He was used as a carrier gas at a flow rate of 40 ml/min and the column temperature was 150° C. Hydrogen was determined by using $N_2$ as carrier gas at a flow rate of 20 ml/min and the column temperature was 60° C. Dissolved $CO_2$ in the medium was calculated from Henry's Law.

The organic acids present in the culture samples were analyzed by HPLC after filtration through a 0.22-$\mu$m Millex filter. A 30 cm×7.8 mm Aminex HPX37H organic acid column (BioRad) was used to separate the organic acids. The eluant was 0.008N $H_2SO_4$. Concentrations of organic acids were determined with a UV detector at 210 nm.

EXAMPLE 3

Solubilization and Bioaccumulation of Lead By Clostridium sp. ATCC 53464

Figure 2:
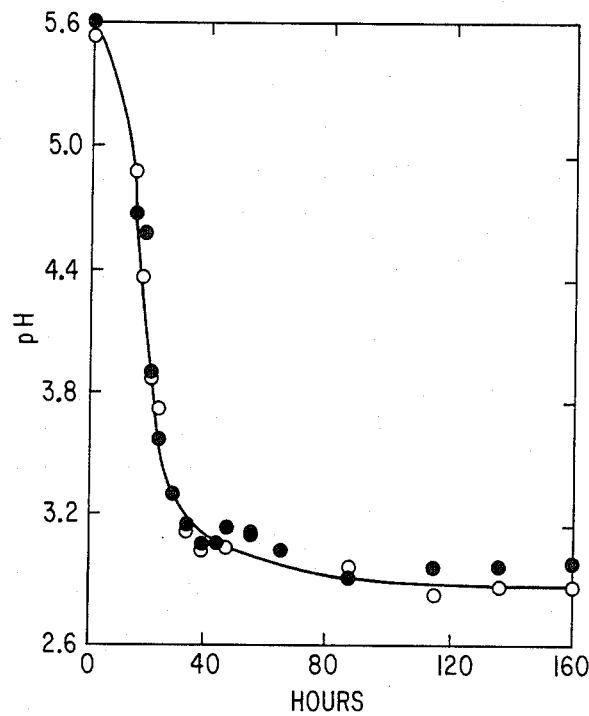
FIG. 2: Change in pH of culture medium by Clostridium sp. ATCC 53464 grown in the presence ( • ) and absence ( ∘ ) of PbO.
Figure 3:
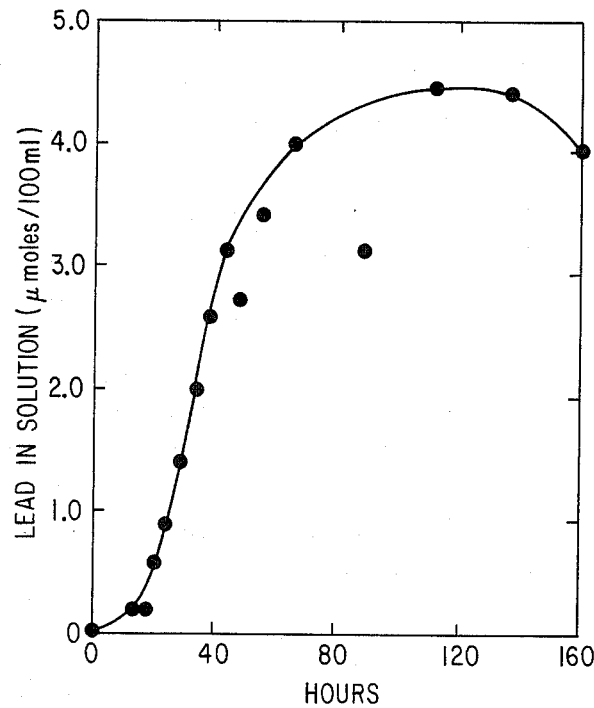
FIG. 3: Dissolution of PbO by Clostridium sp. ATCC 53464 in the culture medium.

To determine the distribution of lead in the cells and in culture supernatant, a culture prepared as in Example 1 was used to which was added 12 $\mu$moles of PbO/100 ml. Control samples were also prepared and grown to which no lead oxide was added. The cultures were grown for 72 hours. Growth of Clostridium sp. ATCC 53464 in the presence and absence of lead oxide is shown in FIG. 1. Growth of the organism was inhibited by about 60% in lead-containing samples. As shown in FIG. 2, the pH of the culture medium with and without lead oxide became acidic as the growth progressed. The concentration of soluble lead in the culture medium, shown in FIG. 3, increased at the rate of approximately 1.34 nmol/ml/hr.

The culture was centrifuged at 3000×g and separated into cell pellet and supernatant. The cell pellet was dried and digested with ultrex $HNO_3$. The supernatant was filtered through a 0.22-$\mu$ filter. Polymer-like material attached to the inside walls of the incubation bottles was digested with Ultrex $HNO_3$ in the bottle. The lead content in the filtered supernatant and in the digested cell pellet and polymer was determined by polarography.

The dissolution of lead oxide due to the action of bacterium ATCC No. 53464 was determined as follows. The bacteria were grown in the presence of 1.97, 5.21, 10.3, and 20.6 $\mu$moles of PbO/40 ml of medium. At late logarithmic growth phase the culture medium was filtered, acidified with Ultrex $HNO_3$, and analyzed for soluble lead.

In a parallel experiment, the bacteria were grown to late logarithmic growth phase in medium without PbO. The cells were separated from the growth medium by filtration and 0, 0.4, 1.3, 2.4, and 4.8 $\mu$moles of PbO were added to 10 ml aliquots of the filtered supernatant and incubated for 48 h. The samples were filtered, acidified, and analyzed for soluble lead. All operations were performed in an anaerobic hood.

After three days incubation of the bacterium ATCC No. 53464 grown in the presence of PbO, approximately 30% of the added lead was found in a soluble form in the culture medium. The final pH of the medium after growth dropped from 6.8 to 3.1±0.1 in all cases due to the production by Clostridium sp. ATCC No. 53464 of acetic, butyric and lactic acids in the presence of lead compounds. The growth of Clostridium sp. ATCC No. 53464, as determined by turbidity and total number of cells (AODC), was only slightly affected in medium containing 4.8 μmoles PbO. However, the growth of the organism was not affected by the acidic pH of the medium.

The effect of the addition of varying concentrations of PbO to culture medium on growth of Clostridium sp. ATCC NO. 53464 and dissolution of PbO is shown in Table 1.

TABLE 1

Dissolution of Lead Oxide by Clostridium sp. ATCC No. 53464

| μmoles PbO/40 ml | Growth (OD) | Soluble Pb found in culture medium μmoles (+ISEM) |
|---|---|---|
| 0 | 0.67 | 0 |
| 1.83 ± .04 | 0.66 | 0.55 ± 0.09 |
| 3.32 ± .07 | 0.66 | 0.92 ± 0.18 |
| 4.84 ± 0.1 | 0.63 | 1.64 ± 0.11 |
| 9.55 ± 0.1 | 0.69 | 2.59 ± 0.22 |
| 19.1 ± 0.1 | 0.51 | 5.49 ± 0.26 |

As can be seen from Table 1, soluble lead present in the culture filtrate increased proportionately with an increase in the concentration of insoluble PbO added to the medium. However, only about 30% of the added lead was detected as soluble lead regardless of the amount of lead added to the medium. This difference may be due to bioaccumulation and immobilization of solubilized lead by microbial biomass. A substantial portion of the solubilized lead is associated with cell biomass as well as with the polymer material and other residues produced by the cells. Table 2 shows the distribution of lead in the culture.

TABLE 2

Distribution of Lead in the Culture

| Fraction | % Pb ± ISEM |
|---|---|
| Filtrate | 26 ± 1 |
| Cell pellet (1.07 ± 0.13 mg dry wt) | 38 ± 1 |
| Fraction adhered to culture bottle | 37 ± 6 |

Dissolution of PbO closely followed the rate of growth as well as change in pH of the growth medium. The pH of the medium changed from 6.4 to 3.2. The rate of Pb dissolution during logarithmic growth of the bacteria in 40 ml of medium containing 3.32 μmoles of PbO was 0.042 μmoles ml$^{-1}$h$^{-1}$. When the bacteria were grown in a buffered medium containing 0.1 g CaCO$_3$ and 4.8 μmoles PbO/40 ml at pH 7, 2.2 nmoles of Pb/ml were detected in the filtrate and the final pH of the medium dropped to 5.3.

Dissolution of the PbO may be due not only to the direct microbial action of Clostridium sp. ATCC No. 53464, but also to indirect action by microbial metabolic products. Dissolution of PbO by cell-free spent medium obtained from cultures grown in the presence and absence of PbO clearly indicates that the components present in the cell-free medium and/or the low pH are partially responsible for dissolution of PbO. The difference between the amount of PbO dissolved by the cell-free spent culture medium and cells grown in the presence of PbO is due to lead immobilization by bacterial biomass.

Analysis of the culture filtrate obtained from cells grown in media without lead oxide showed the presence of acetic and butyric acids as major metabolites. A similar analysis of the culture filtrate obtained from cells grown in media with lead oxide showed the presence of not only acetic and butyric acids but also lactic acid (see Table 3).

TABLE 3

Organic Acid Production By Clostridium sp. ATCC No. 53464 Grown in the Presence and Absence of Lead Oxide

| Organic Acid (μmoles/40 ml ± ISEM) | Addition | |
|---|---|---|
| | None | PbO (4.8 μmoles) |
| Acetic Acid | 252 ± 13 | 172 ± 9 |
| Butyric Acid | 440 ± 27 | 397 ± 8 |
| Lactic Acid | ND | 131 ± 8 |
| Total | 702 ± 40 | 712 ± 12 |

Figure 4:
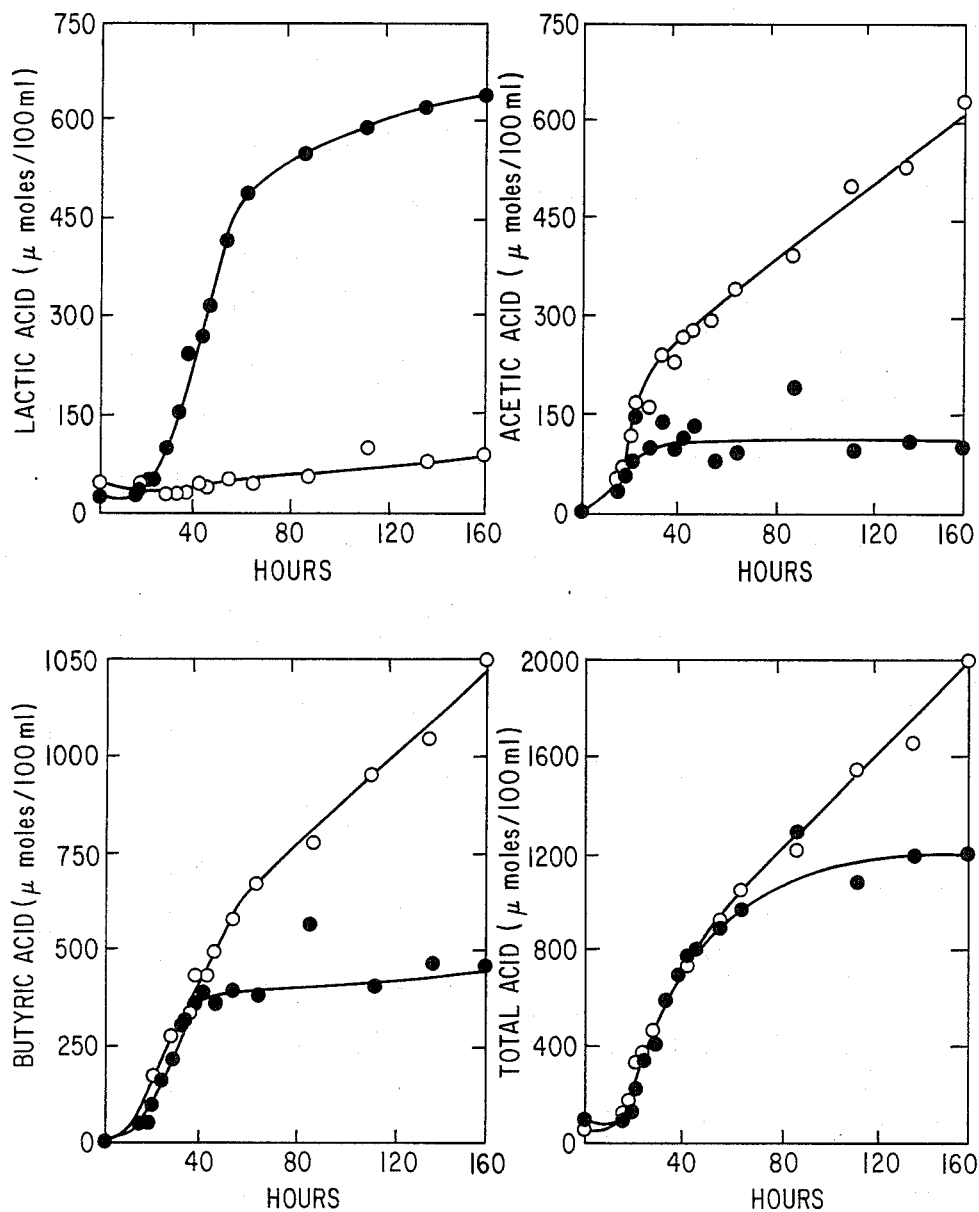
FIG. 4: Production of organic acids by Clostridium sp. ATCC 53464 in the presence ( • ) and absence ( ∘ ) of PbO.

FIG. 4 shows in more detail acetic, butyric and lactic acid production by Clostridium sp. ATCC 53464 in the presence and absence of lead oxide. The rate of acetic acid accumulation during the logarithmic growth of the organism in samples with and without PbO was 10 and 90 nmol/ml/hr, respectively. In samples containing PbO, butyric acid production exceeded acetic acid production and continued long after acetic acid accumulation ceased. However, the rate of butyric acid production (140 nmol/ml/hr) during logarithmic growth of the organism in samples either with or without PbO showed no significant difference. Lactic acid was produced at the rate of 120 nmol/ml/hr in PbO-containing samples, while 0.5 nmol/ml/hr was produced in samples without PbO. Increase in lactic acid production was commensurate with an increase in solubilized lead in the growth medium. Differences in the total organic acid production between samples with and without PbO were evident after 50 hr, with a 40% decrease in PbO-containing samples after 160 hr.

EXAMPLE 4

Addition of Iron To Fermentation Medium

The fermentation pattern of glucose was influenced not only by the presence of soluble lead but also by the amount of iron initially added to the medium. Therefore, the effect of addition of varying concentrations of iron in the presence and absence of PbO on the growth and fermentation pattern of glucose by Clostridium sp. ATCC 53464 was examined after 48 hr of incubation.

The data in Table 3 below show that the iron requirement for maximum growth of the organism was 0.3 μmol per 100 ml under the test conditions. Variations in maximum growth as determined by OD between FIG. 1 and Table 3 are possibly due to the differences in the iron content of the medium. The iron concentration was carefully controlled. The organism grew poorly at the lower iron concentrations tested. No increase in growth of the organism was observed when iron concentration in the medium was increased to 10 μmol/100 ml. However, addition of PbO significantly affected the growth of the organism at Fe concentration up to 0.3 μmol/100 ml and normal growth was reestablished when the iron content of the medium was increased to 1.0 μmol/100 ml. These results suggest that the effect of solubilized lead on growth of the organism can be overcome by supplementing the growth medium with excess iron. Thus, by adding iron to the growth medium used to solubilize the lead oxide, the growth rate of the organism and thus its efficiency in solubilizing the lead oxide is increased.

Dissolution of PbO was dependent upon growth, quantity of organic acids produced, and the final pH of the growth medium. Addition of 0 to 1.0 μmol of iron/100 ml of medium stimulated growth of the organism with a concurrent increase in soluble Pb in the culture medium. About 30 to 55% of the added lead (12.4 μmol/100 ml) was seen as soluble lead, and the final pH of the medium varied from 3.56 with no added iron to 3.20 with the addition of 1.0 μmol of iron. At 0 and 0.005 μmol Fe additions, the soluble lead in the culture medium was 3.8±0.3 and 5.3±0.2 μmol/100 ml, respectively. At higher iron concentrations (0.05, 0.3 and 1 μmol/100 ml) 6.0±0.1 to 7.0±0.2 μmol of lead were detected in the culture medium.

TABLE 3

Effect of iron on growth of Clostridium sp. ATCC 53464 in the presence and absence of lead oxide

| Fe (μmol per 100 ml)[a] | Growth (OD at 600 nm) | |
| --- | --- | --- |
| | No PbO | PbO |
| 0 | 0.33 | 0.14 |
| 0.005 | 0.33 | 0.22 |
| 0.05 | 0.50 | 0.33 |
| 0.3 | 0.75 | 0.55 |
| 1.0 | 0.76 | 0.75 |

[a]Growth medium contained all ingredients except iron which was added to the medium as indicated.

What is claimed is:

1. A method of solubilizing lead oxide in industrial wastes and producing soluble $Pb^{2+}$ which comprises dissolving said lead oxide by contacting said wastes with an anaerobic bacterial culture containing Clostridium sp. ATCC No. 53464 before said wastes are dumped into the environment, and removing the solubilized lead from the wastes by chemical separation and bioaccumulation.

2. The method according to claim 1 wherein acetic, butyric, and lactic acids are produced as metabolites producing an acid dissolution medium.

3. The method according to claim 1 wherein iron is added to said bacterial culture.

4. A method of producing lactic acid which comprises growing Clostridium sp. ATCC No. 53464 under anaerobic conditions in a growth medium to which lead oxide has been added.

* * * * *